(12) United States Patent
Butch et al.

(10) Patent No.: US 11,147,557 B1
(45) Date of Patent: Oct. 19, 2021

(54) SURGICAL CLIP APPLICATOR

(71) Applicant: ZSX Medical, LLC, Philadelphia, PA (US)

(72) Inventors: Jesse Butch, Philadelphia, PA (US); Dan Mazzucco, Haddon Heights, NJ (US); John Crombie, East Hanover, NJ (US); Vincent Biondo, Flemington, NJ (US)

(73) Assignee: ZSX MEDICAL, LLC, Philadelphia, PA (US)

( * ) Notice: Subject to any disclaimer, the term of this patent is extended or adjusted under 35 U.S.C. 154(b) by 77 days.

(21) Appl. No.: 16/680,999

(22) Filed: Nov. 12, 2019

Related U.S. Application Data

(60) Provisional application No. 62/757,860, filed on Nov. 9, 2018.

(51) Int. Cl.
*A61B 17/10* (2006.01)
*A61B 17/00* (2006.01)
*A61B 17/08* (2006.01)

(52) U.S. Cl.
CPC ........ *A61B 17/10* (2013.01); *A61B 17/00234* (2013.01); *A61B 17/083* (2013.01); *A61B 2017/0042* (2013.01); *A61B 2017/00367* (2013.01)

(58) Field of Classification Search
CPC .... A61B 2017/2932; A61B 2017/2939; A71B 17/083; A71B 17/10; A71B 17/072; A71B 17/07207; A71B 17/2909; A71B 17/122
See application file for complete search history.

(56) References Cited

U.S. PATENT DOCUMENTS

| 9,358,008 B2 | 6/2016 | Mazzucco et al. |
| 2010/0089970 A1* | 4/2010 | Smith .................. A61B 17/068 227/175.1 |

* cited by examiner

*Primary Examiner* — Majid Jamialahmadi
(74) *Attorney, Agent, or Firm* — Panitch Schwarze Belisario & Nadel LLP

(57) ABSTRACT

An applicator for applying a surgical clip to a patient's tissue has a frame assembly with an applicator tube having a distal end configured to releasably receive the surgical clip. The applicator has a surgical-clip opening assembly including a clip-opening trigger, a clip-opening rod disposed in the applicator tube and a clip-opening jaw. Activation of the clip-opening trigger displaces the clip-opening rod proximally opening the clip-opening jaw. A surgical-clip closing assembly has a clip-closing trigger, a clip-closing rod disposed in the applicator tube and a clip-closing beam. Activation of the clip-closing trigger displaces the clip-closing rod distally closing the clip-opening jaw. A surgical-clip ejection assembly has a clip ejection knob, a clip-ejection rod disposed in the applicator tube and a clip ejection beam. Activation of the clip-ejection knob ejects the surgical clip. The clip-opening trigger, clip-closing trigger and clip ejection knob are independently activatable.

11 Claims, 15 Drawing Sheets

SURGICAL CLIP APPLICATOR

CROSS-REFERENCE TO RELATED APPLICATIONS

This application claims the benefit of U.S. Provisional Patent Application No. 62/757,860, filed Nov. 9, 2018, the entirety of which is incorporated herein by reference.

BACKGROUND OF THE INVENTION

Embodiments of the present invention relate generally to surgical clip applicators, and more particularly, to laparoscopic surgical clip applicators.

Recently, surgical clips have been developed for use in the effective and efficient closing of surgical wounds. The use of such clips in place of, for example, sutures, staples, tapes, adhesives, sealants, and the like decreases overall surgical procedure time and reduces the risk of post-operative infection. These clips are described in U.S. Pat. No. 9,358,008 B2, the entirety of which is incorporated herein by reference.

It is desirable to provide applicators for these and other types of surgical clips that enable simple and efficient application of the clips to the wound site in the patient's tissue

BRIEF SUMMARY OF THE INVENTION

Briefly stated, one embodiment of the present invention is directed to a surgical-clip applicator for applying a surgical clip to a patient's tissue. The applicator comprises a frame assembly, a surgical-clip opening assembly, a surgical-clip closing assembly, and a surgical-clip ejection assembly. The frame assembly comprises an applicator tube having an applicator-tube proximal end and an applicator-tube distal end. The applicator-tube proximal end is attached to the frame assembly; the applicator-tube distal end is configured to releasably receive and discharge the surgical clip. The surgical-clip opening assembly comprises a clip-opening trigger, a clip-opening rod, and a clip-opening jaw. The clip-opening trigger is operatively coupled to the frame assembly. The clip-opening rod has a clip-opening-rod proximal end and a clip-opening-rod distal end. The clip-opening rod is disposed in the applicator tube. The clip-opening-rod proximal end is operatively coupled to the clip-opening trigger. The clip-opening jaw is operatively coupled to the applicator-tube distal end and the clip-opening-rod distal end. Activation of the clip-opening trigger causes displacement of the clip-opening rod proximally opening the clip-opening jaw. The surgical-clip closing assembly comprises a clip-closing trigger, a clip-closing rod, and a clip-closing beam. The clip-closing trigger has a clip-closing-trigger upper end and a clip-closing-trigger lower end. The clip closing trigger is operatively coupled to the frame assembly. The clip-closing rod has a clip-closing-rod proximal end and a clip-closing-rod distal end. The clip-closing rod is disposed in the applicator tube. The clip-closing-rod proximal end is operatively coupled to the clip-closing trigger. The clip-closing beam is attached to the clip-closing-rod distal end. Activation of the clip-closing trigger causes displacement of the clip-closing rod distally causing the clip-closing beam to close the clip-opening jaw. The surgical-clip ejection assembly comprises a clip-ejection knob, a clip-ejection rod and a clip-ejection beam. The clip-ejection knob is slideably disposed on the clip-closing rod and has a clip-ejection-knob tab operatively coupled to the frame assembly. The clip-ejection rod has a clip-ejection-rod proximal end and a clip-ejection-rod distal end. The clip-ejection rod is disposed in the applicator tube. The clip-ejection-rod proximal end is operatively coupled to the clip-ejection knob. The clip-ejection beam is attached to the clip-ejection-rod distal end. Activation of the clip-ejection-knob tab causes displacement of the clip-ejection beam distally ejecting the surgical clip from the applicator when the surgical clip is releasably retained in the applicator-tube distal end. The surgical-clip opening assembly, the surgical-clip closing assembly, and the surgical-clip ejection assembly are independently activatable.

BRIEF DESCRIPTION OF THE SEVERAL VIEWS OF THE DRAWINGS

The following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
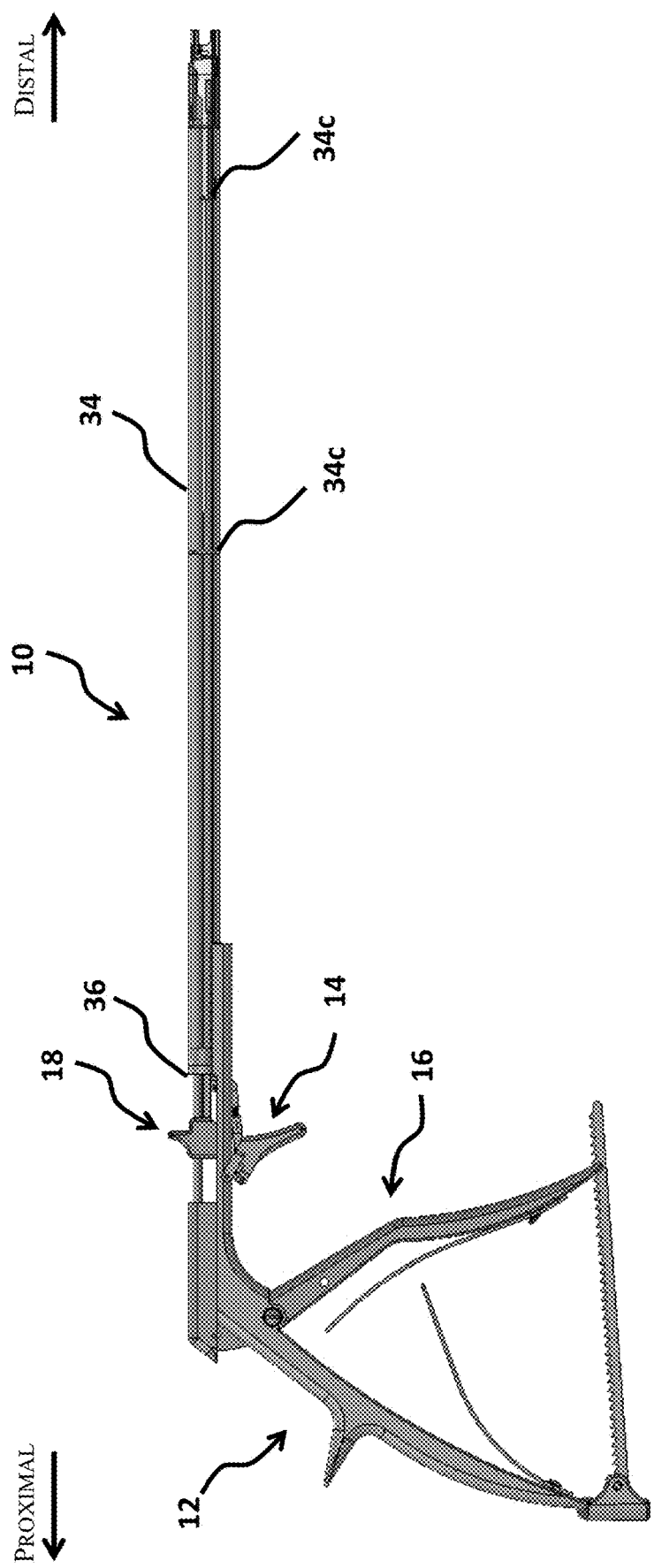
FIG. 1 is right-side elevation view of the surgical tool applicator in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the surgical clip applicator and designated parts thereof. The terminology includes the words noted above, derivatives thereof and words of similar import.

Referring to the drawings in detail, where like numerals indicate like elements throughout, there is shown in FIGS. 1-19 a first preferred embodiment of a surgical clip applicator generally designated 10 and hereafter referred to as the "applicator 10" for the application of a compressive surgical clip 1 at a surgical site to close a surgical incision. The surgical clip applied by the applicator 10 is preferably, but not necessarily, substantially the same as the surgical clip 1 shown in FIGS. 20 and 21A-21G and disclosed in U.S. Pat. No. 9,358,008 B2. The clip 1 includes a first clamping arm 2, a second clamping arm 3, and a flexible pin 4 maintained between the first and second clamping arms 2, 3 in a press-fit relationship. Each of the first and second clamping arms 2, 3 has a proximal first end 2a, 3a, an opposing distal second end 2b, 2c and a sidewall 2c, 3c extending therebetween. The clip 1 has a first position P1 in which the proximal first ends 2a, 3a of the first and second clamping arms 2, 3 partially engage or do not engage each other and a second position P2 in which the proximal first ends 2a, 3a of the first and second clamping arms 2, 3 pivotally engage each other. In the second position P2 of the clip 1, a compressive force F generated at the proximal first ends 2a, 3a is transferred through the first and second clamping arms 2, 3 to the distal second ends 2b, 3b, as further described below.

The applicator 10 has a hand-gun style frame assembly 12 to which a surgical-clip opening assembly 14, a surgical-clip closing assembly 16 and a surgical-clip ejection assembly 18 are independent and operatively coupled to the frame assembly 12.

Figure 4:
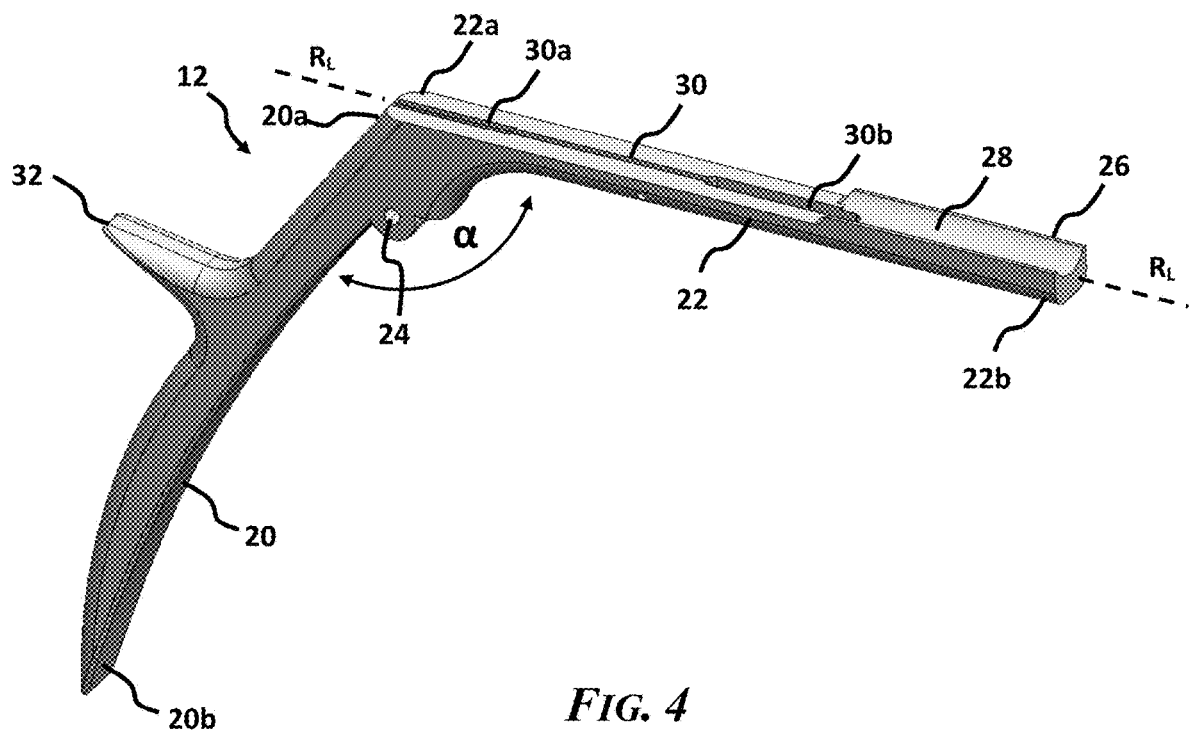
FIG. 4 is a front, right-side perspective view of the frame assembly of the surgical tool applicator of FIG. 1.
Figure 5:
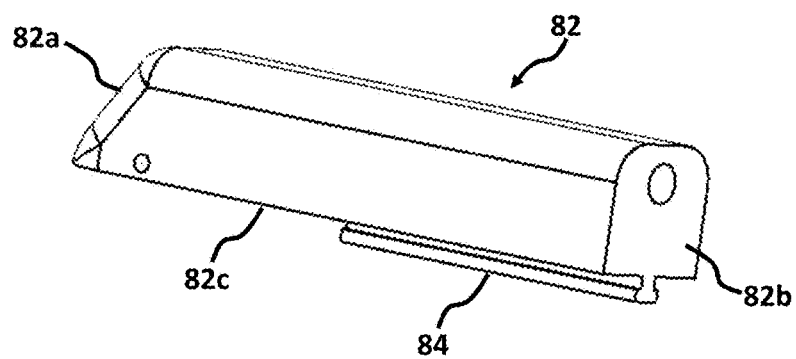
FIG. 5 is a front, right-side perspective view of the slider of the clip-closing assembly of the surgical tool applicator of FIG. 1.

Referring to FIG. 4, the frame assembly 12 includes a frame-assembly hand grip 20 having a frame-assembly hand-grip upper end 20a from which the proximal end 22a of a frame-assembly rail 22 extends along a longitudinal rail axis $R_L$ at an obtuse angle α relative to the frame-assembly hand grip 20. A hinge joint 24, or similar joint that allows for pivotal motion, is provided adjacent the vertex formed by the frame-assembly hand-grip upper end 20a and the frame-assembly rail proximal end 22a. The frame-assembly rail distal-end portion 26 has a generally concave rail upper surface 28. A frame-assembly rail slot 30 extends longitudinally from the concave rail upper surface 28 to the rail proximal end 22a. A thumb rest 32 projects proximally from the mid-section of the frame-assembly hand grip 20.

An applicator tube 34 extends beyond the rail distal end 22b. The applicator-tube proximal end 34a is fixedly attached to the concave rail upper surface 28 by a weldment, or substantially equivalent bonding technique, and is sealed by an applicator-tube plug 36. (See FIGS. 1 and 3). Preferably, the applicator-tube distal end 34b is configured as a removable applicator-tube tip 38 (see, FIGS. 8, 9 and 24) having an applicator-tube tip proximal end 38a attachable to the distal end 34b of the applicator tube 34 and an applicator-tube tip distal end 38b configured to receive surgical clips having a corresponding configuration. For example, one applicator-tube tip may have a distal end configured to releasably receive surgical clips having the configuration of the surgical clip 1; alternatively, other applicator-tube tips may have a distal end configured to releasably receive surgical clips having a configuration differing from the configuration of the surgical clip 1. Applicator-tube alignment pins 34c, both horizontal and vertical, may be provided to support contents within the applicator-tube 34.

In some embodiments, the applicator tip may not be releasably attached to the applicator-tube distal end; instead, the applicator-tube distal end 34b may be die-formed, injection molded or machined to have a configuration able to receive a desired surgical clip 1.

Figure 2:
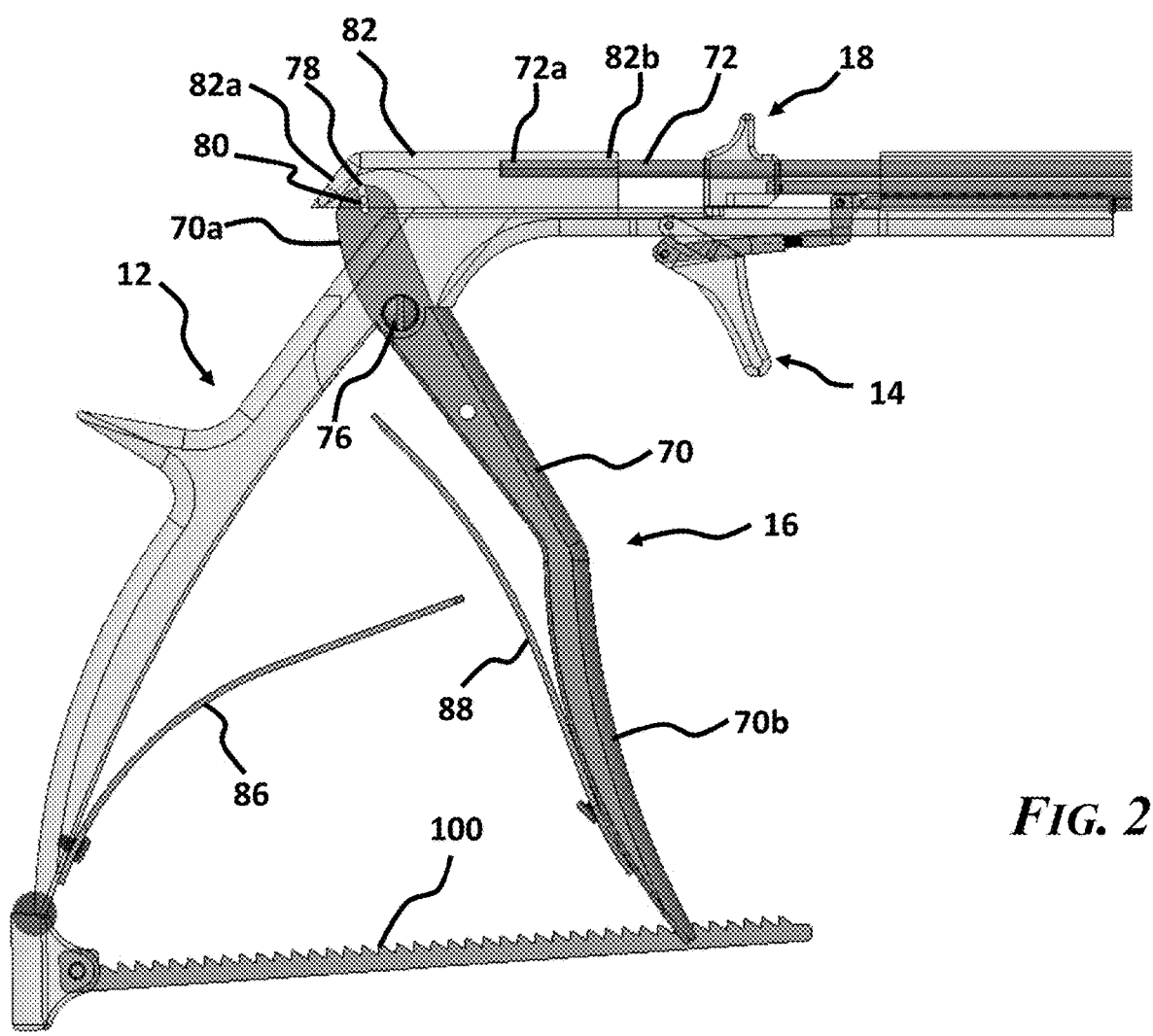
FIG. 2 is right-side elevation view of a proximal portion of the surgical tool applicator of FIG. 1 with the frame assembly shown in transparency.
Figure 3:
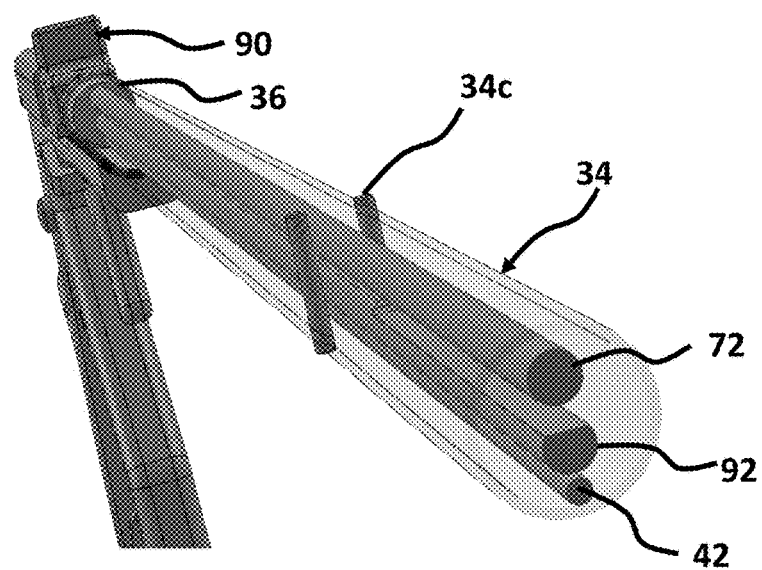
FIG. 3 is a front, right-side perspective cross-sectional view of a proximal portion of the surgical tool applicator of FIG. 1 with the applicator tube shown in transparency.
Figure 6:
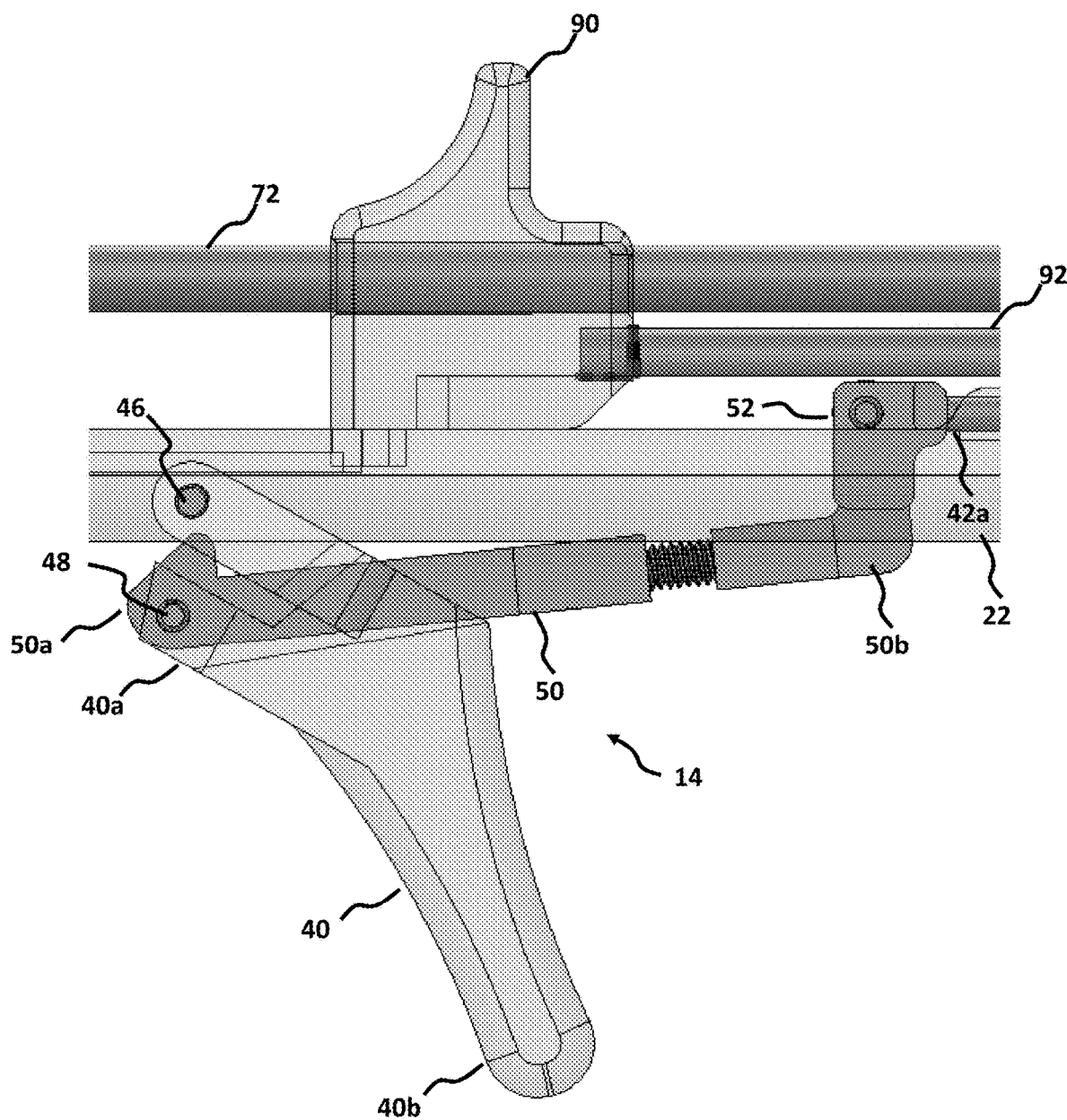
FIG. 6 is a right-side elevation view of a portion of the mid-section of the surgical tool applicator of FIG. 1 with the clip-opening trigger, clip-ejection knob and the frame-assembly rail shown in transparency.
Figure 7:
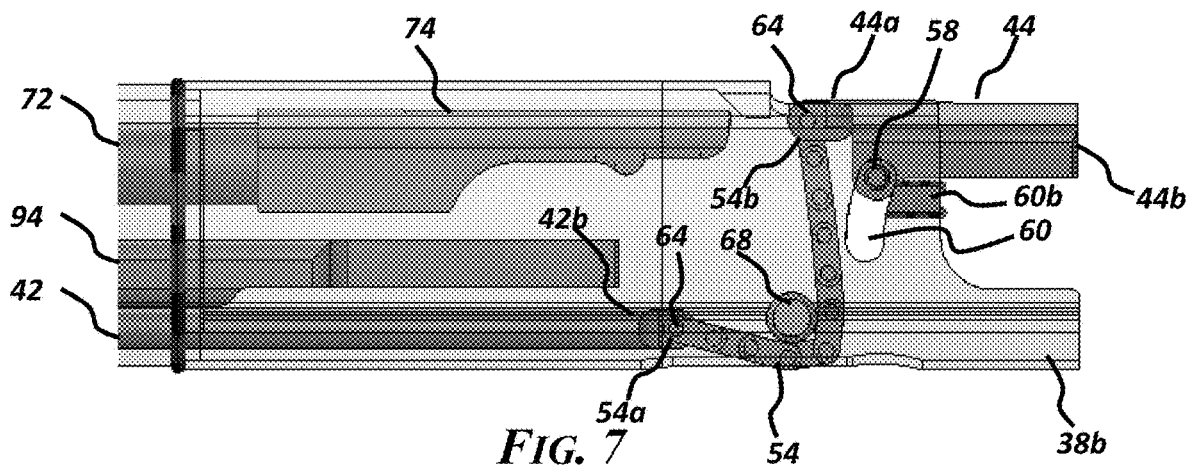
FIG. 7 is a right-side elevation view of the distal end of the surgical tool applicator of FIG. 1 with the applicator-tube tip shown in transparency.
Figure 8:
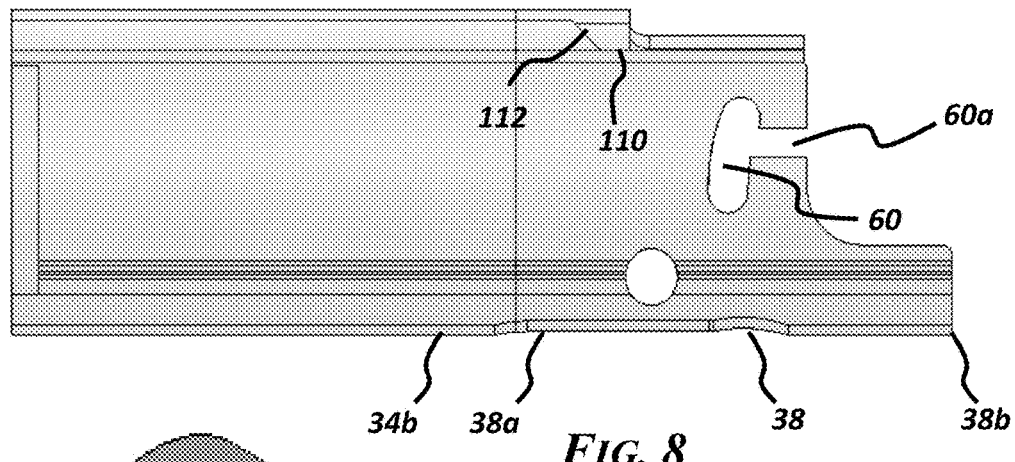
FIG. 8 is a right-side elevation view in cross section of the applicator-tube tip of the surgical tool applicator of FIG. 1.
Figure 9:
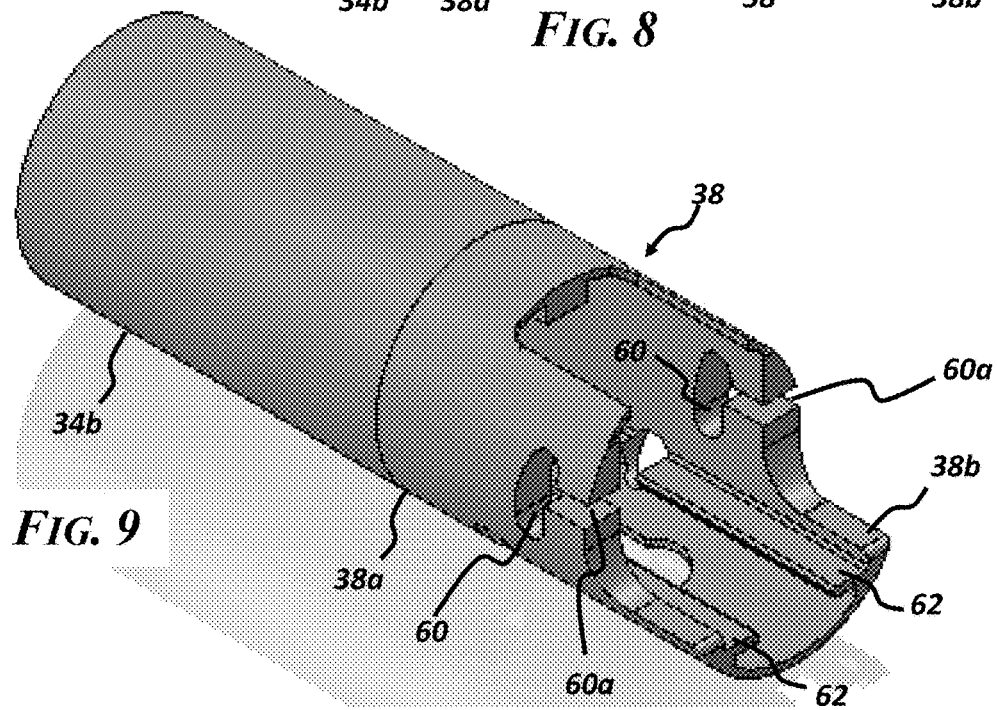
FIG. 9 is a right-side top perspective view of the distal end of the applicator-tube tip of the surgical tool applicator of FIG. 1.
Figure 10:
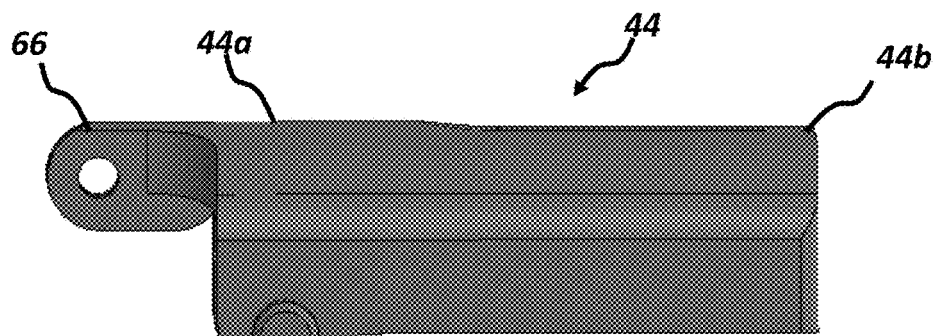
FIG. 10 is a right-side elevation view of the clip-opening jaw of the surgical tool applicator of FIG. 1.
Figure 11:
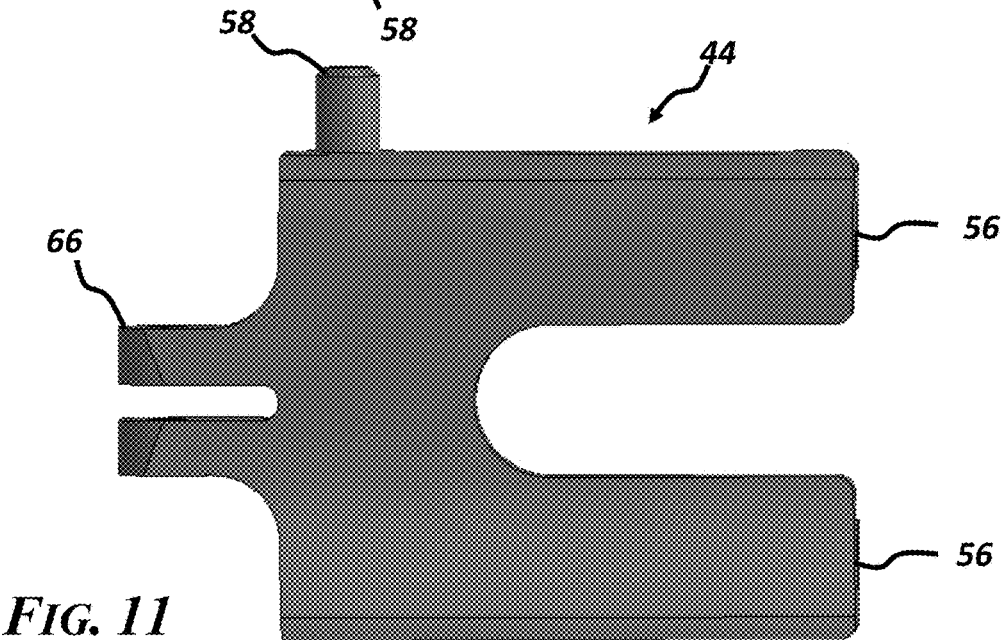
FIG. 11 is a top plan view of the clip-opening jaw of the surgical tool applicator of FIG. 1.
Figure 12:
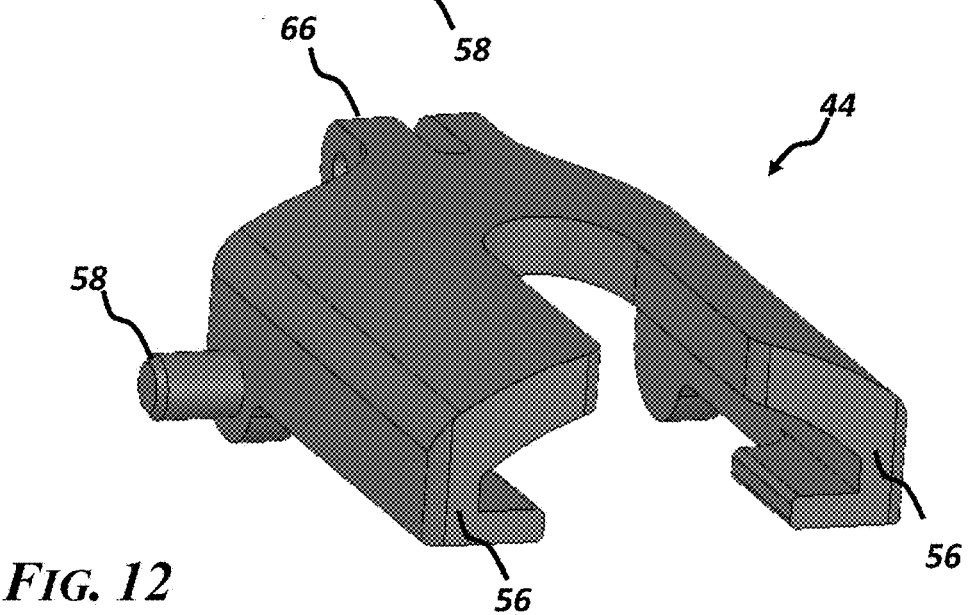
FIG. 12 is a right-side top front perspective view of the clip-opening jaw of the surgical tool applicator of FIG. 1.
Figure 13:
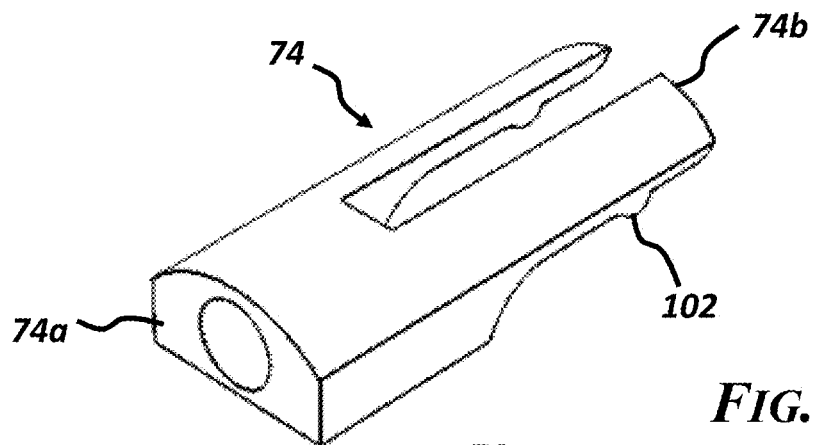
FIG. 13 is a right-side top rear perspective view of the clip-closing beam of the surgical tool applicator of FIG. 1.
Figure 14:
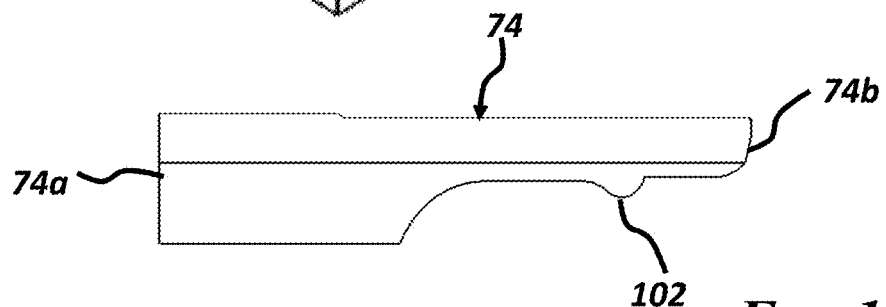
FIG. 14 is a right-side elevation view of the clip-closing beam of the surgical tool applicator of FIG. 1.
Figure 15:
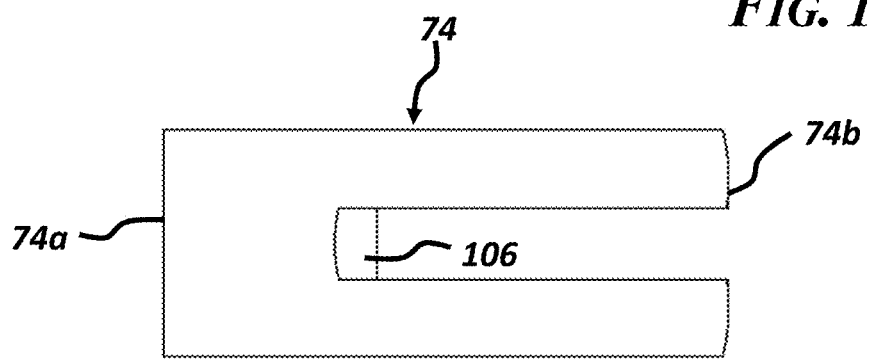
FIG. 15 is a top plan view of the clip-closing beam of the surgical tool applicator of FIG. 1.
Figure 16:
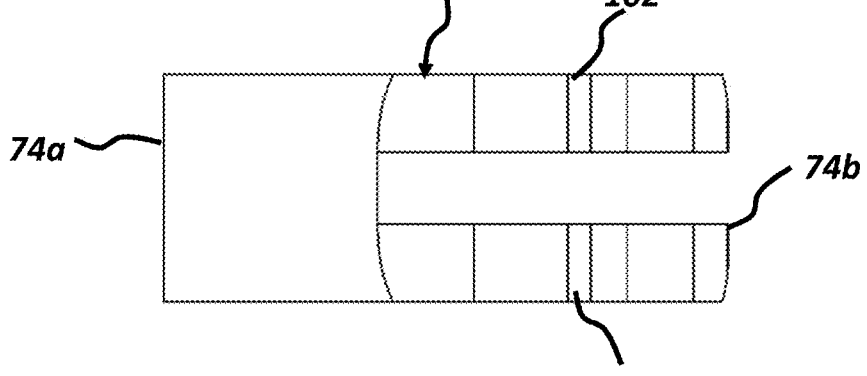
FIG. 16 is a bottom plan view of the clip-closing beam of the surgical tool applicator of FIG. 1.
Figure 17:
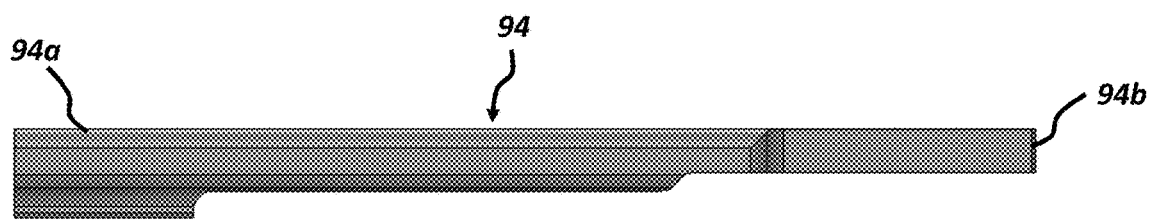
FIG. 17 is a right-side elevation view of the clip-ejection beam of the surgical tool applicator of FIG. 1.
Figure 18:
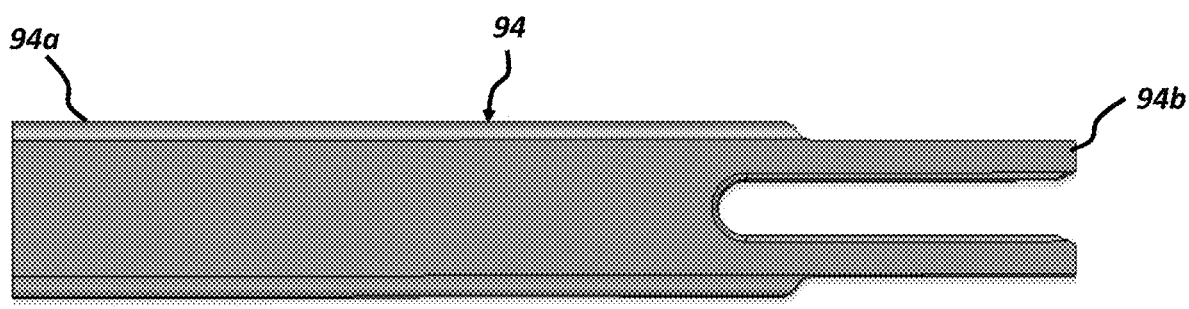
FIG. 18 is a top plan view of the clip-ejection beam of the surgical tool applicator of FIG. 1.
Figure 19:
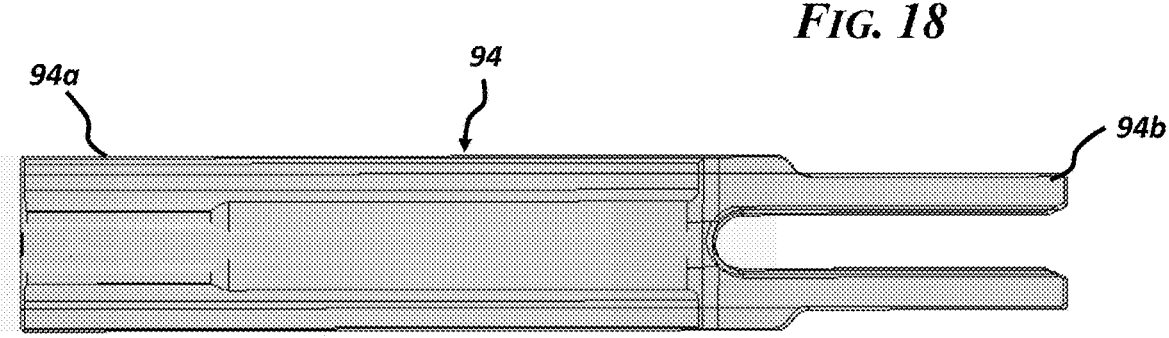
FIG. 19 is a bottom plan view of the clip-ejection beam of the surgical tool applicator of FIG. 1.

Referring to FIGS. 2, 6 and 7, the surgical-clip opening assembly 14 comprises a clip-opening trigger 40, a clip-opening rod 42 and a clip-opening jaw 44. The clip-opening trigger 40 has a generally dog-leg-like shape. The upper end portion 40a of the clip-opening trigger 40 has first and second spaced apart clip-opening trigger hinge joints 46, 48 allowing the clip-opening trigger upper end portion 40a to be pivotably attached to the frame-assembly rail 22 by the first clip-opening trigger hinge joint 46 and to the proximal end 50a of a clip-opening trigger link 50 by the second clip-opening trigger hinge joint 48.

Figure 26:
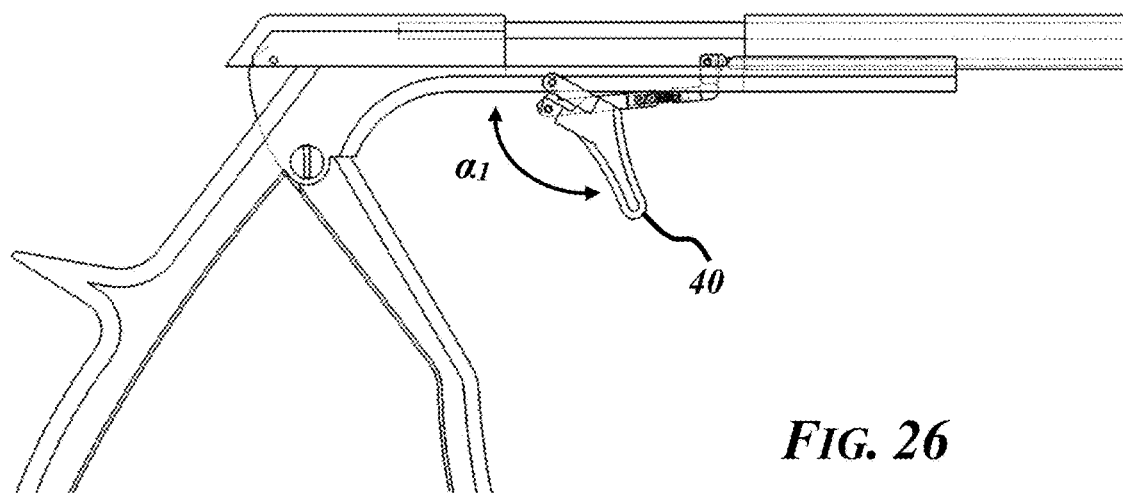
FIG. 26 is a right-side cross-sectional elevation view of a proximal portion of the surgical tool applicator of FIG. 1 showing the clip-opening trigger functioning as a toggle clamp in an unclamped position.
Figure 27:
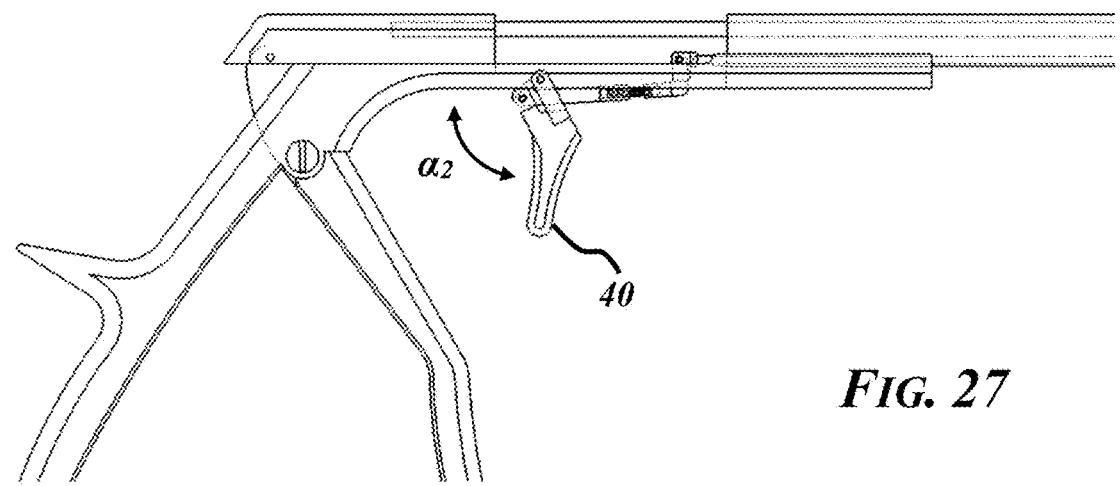
FIG. 27 is a right-side cross-sectional elevation view of a proximal portion of the surgical tool applicator of FIG. 1 showing the clip-opening trigger functioning as a toggle clamp in a central position.
Figure 28:
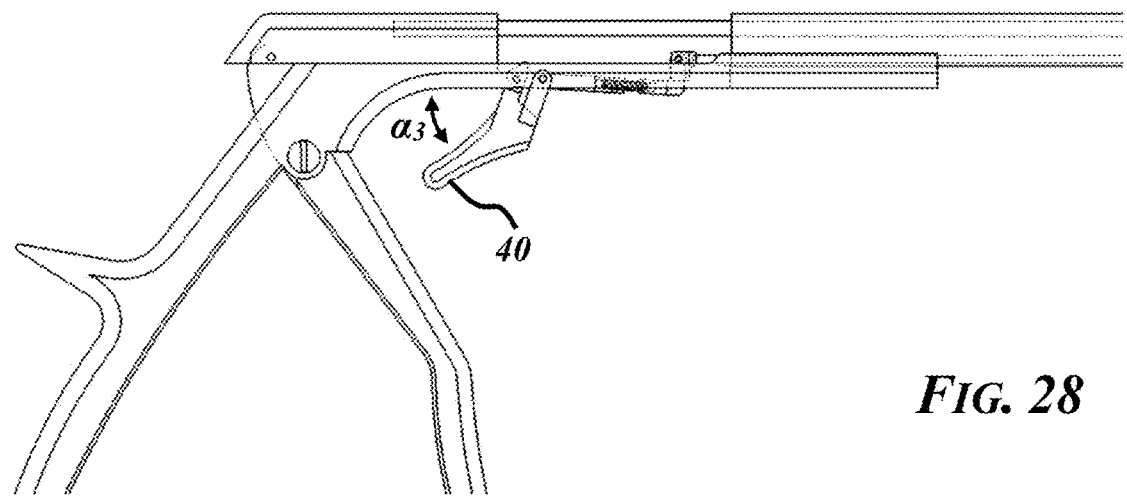
FIG. 28 is a right-side cross-sectional elevation view of a proximal portion of the surgical tool applicator of FIG. 1 showing the clip-opening trigger functioning as a toggle clamp in an over-center, locked position.

In some embodiments, the clip-opening trigger 40 may function as a toggle clamp having an unclamped position $α_1$ shown in FIG. 26 in which no force is applied by the clip-opening trigger 40 to the clip-opening jaw 44, a central position $α_2$ shown in FIG. 27 in which a force applied to the clip-opening trigger 40 opens the clip-opening jaw 44 and an over-center, clamped position as shown in FIG. 28 in which the clip-opening trigger 40, and the clip-opening jaw 44 in turn, are locked in the open position.

The distal end 50b of the clip-opening trigger link 50 is coupled by a clip-opening rod adapter 52 slidably disposed in and projecting downwardly and outwardly through the distal end 30b of the frame-assembly rail slot 30 to the proximal end 42a of a clip-opening rod 42 projecting proximally through the applicator tube plug 36. The clip-opening rod 42, disposed in and extending the length of the applicator tube 34, has a distal end 42b terminating in the applicator tube tip 38. The distal end 42b of the clip-opening rod 42 is operatively coupled to the clip-opening jaw 44 by a flexible link, such as the multi-link chain 54 as further disclosed below. Alternatively, in some embodiments, the flexible link may be a cable, a super elastic material such as nitinol, another flexible member, a bell crank linkage, or another single rigid linkage that achieves the same mechanical motion.

Referring to FIGS. 7-12, the clip-opening jaw 44 is a beamed structure having spaced-apart clip-opening-jaw prongs 56 extending distally. The spaced-apart prongs 56 are configured to releasably receive the first clamping arm 2 of the surgical clip 1. Clip-opening jaw pivot pins 58 extending outwardly from each prong 56 engage diametrically-opposed circumferentially-elongated arcuate slots 60 in the side wall of the applicator-tube tip 38. During assembly, the clip-opening jaw pivot pins 58 are inserted in the arcuate slots 60 through a longitudinal arcuate-slot channel 60a in the applicator-tube tip 38. Thereafter, a channel plug 60b may be fixedly secured in the arcuate-slot channel 60a to retain the clip-opening jaw pivot pins 58 in the arcuate slots 60. The pivot pins float freely in the wall of the applicator tube except during clip ejection (when they contact the wall of the tube) The arcuate slots 60 are spaced from the distal end 38b of the applicator-tube tip 38 such that the clip-opening-jaw prongs 56 are in register with corresponding diametrically-opposed mounts 62 extending inwardly from the side wall of the applicator-tube tip 38 and configured to form a fixed jaw releasably receiving the second clamping arm 3 of the surgical clip 1. The multi-link chain 54 has a multi-link chain distal end 54b attached by a chain hinge pin 64 to a clip-opening-jaw proximal tab 66 extending proximally from the proximal end 44a of the clip-opening jaw 44. The multi-link chain 54 extends within the applicator-tube tip 38 to and around a tip cross pin 68 diametrically opposed to the chain hinge pin 64 and is attached to the distal end 42b of the clip-opening rod 42 by another chain hinge pin 64.

Figure 20:
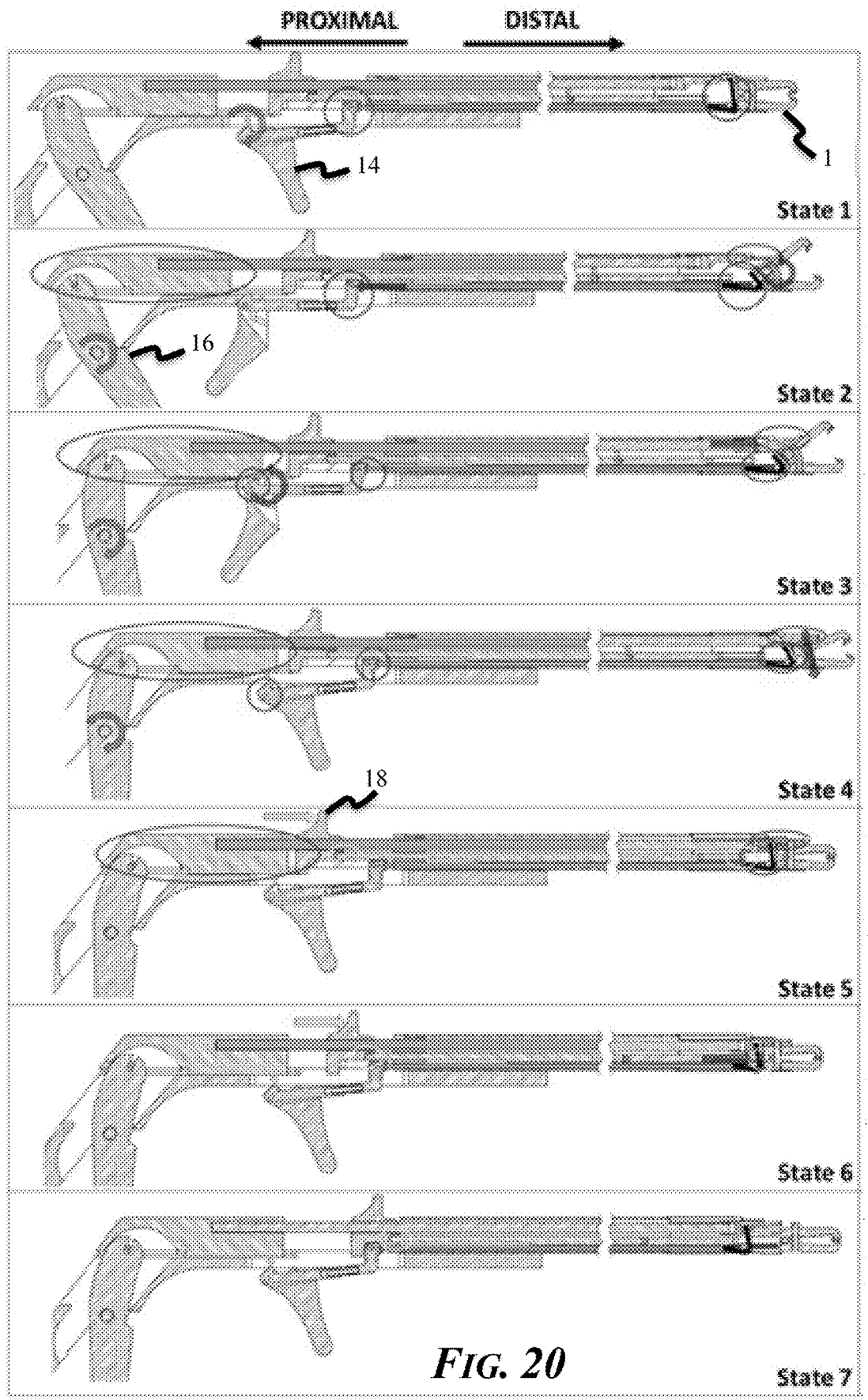
FIG. 20 is an actuation state diagram for the surgical tool applicator of FIG. 1.
Figure 21A:
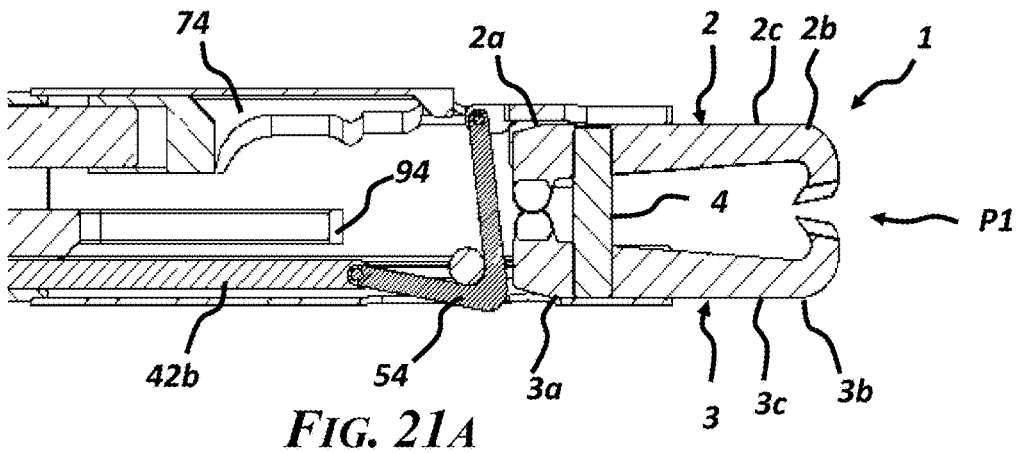
FIGS. 21A-21G are enlarged cross-sectional elevation views of a portion of the distal end of the surgical tool applicator corresponding to the actuation states of FIG. 20.
Figure 21B:
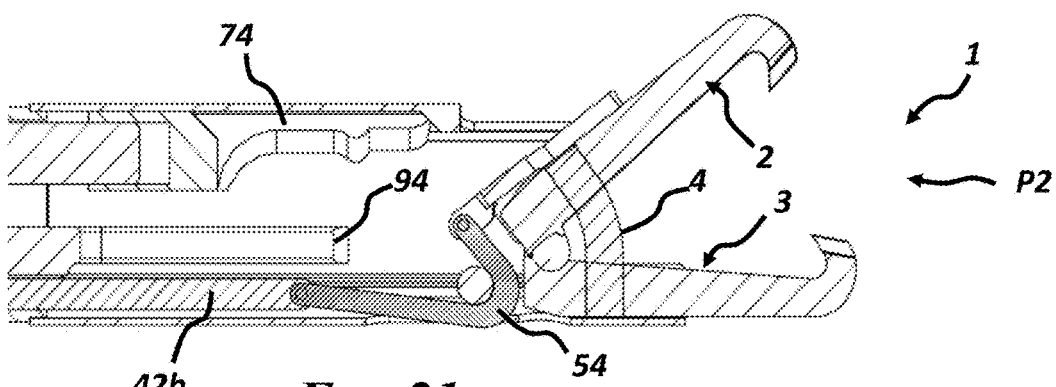
Figure 21C:
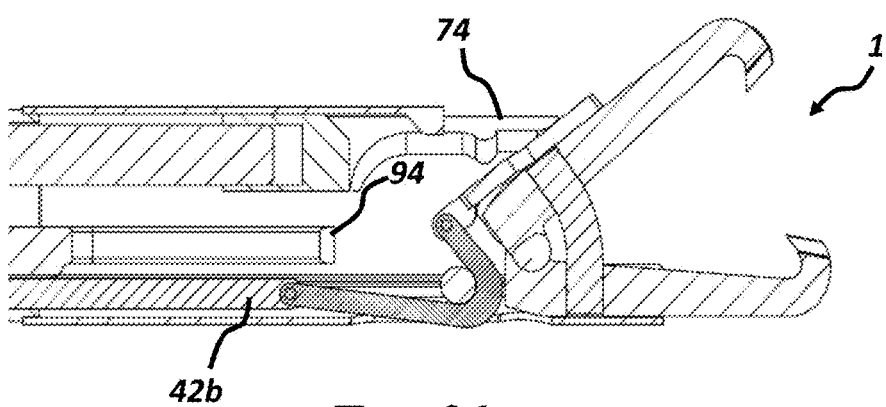
Figure 21D:
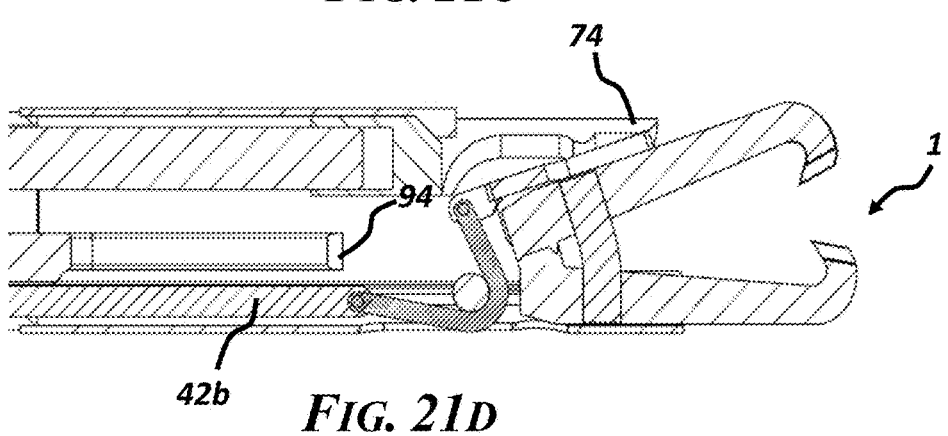
Figure 21E:
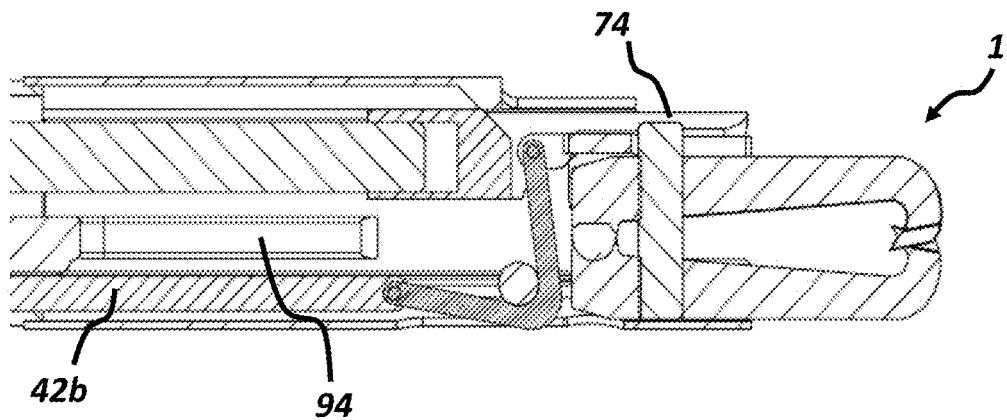
Figure 22A:
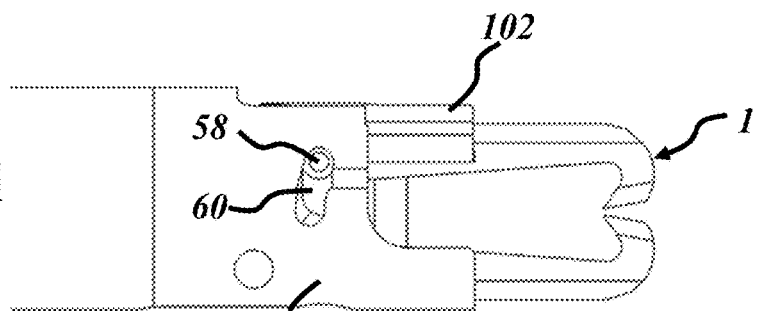
FIGS. 22A-22E are enlarged cross-sectional elevation views of a portion of the distal end of the surgical tool applicator showing the positions of the clip-opening jaw pivot pin in the applicator-tube tip elongated arcuate slot respectively corresponding to the position of the clip-opening jaw in FIGS. 21A-21E.
Figure 22B:
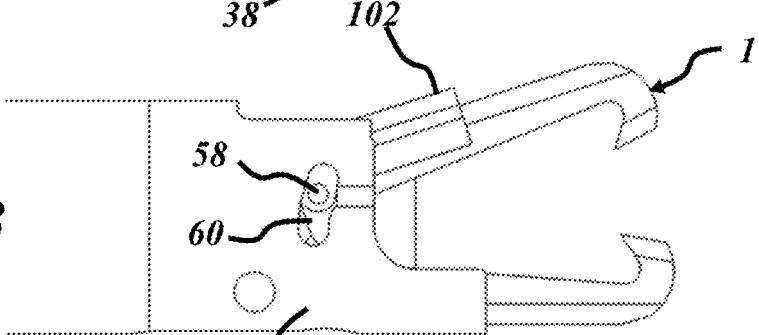
Figure 22C:
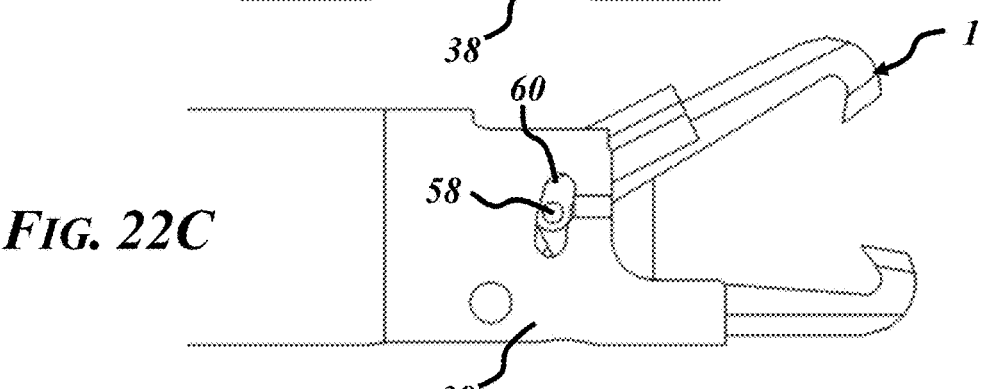
Figure 22D:
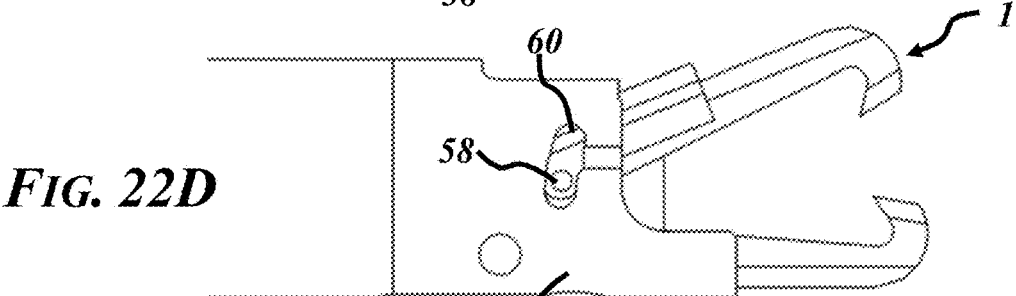
Figure 22E:
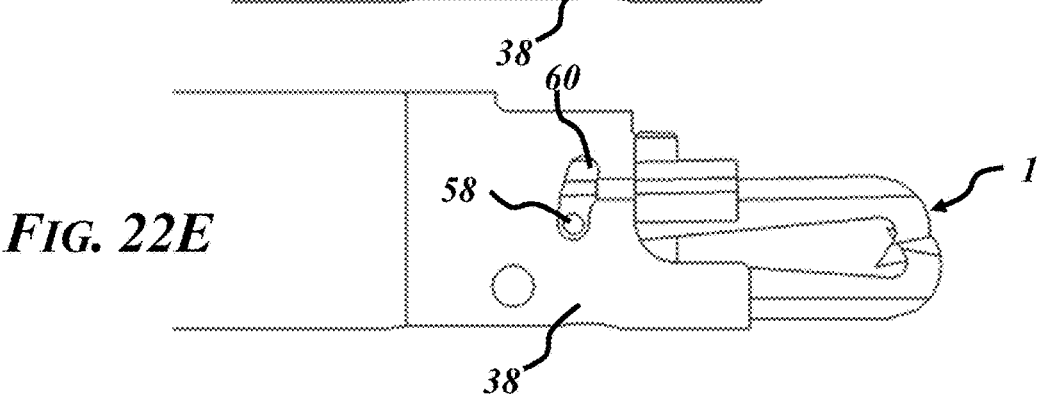
Figure 23:
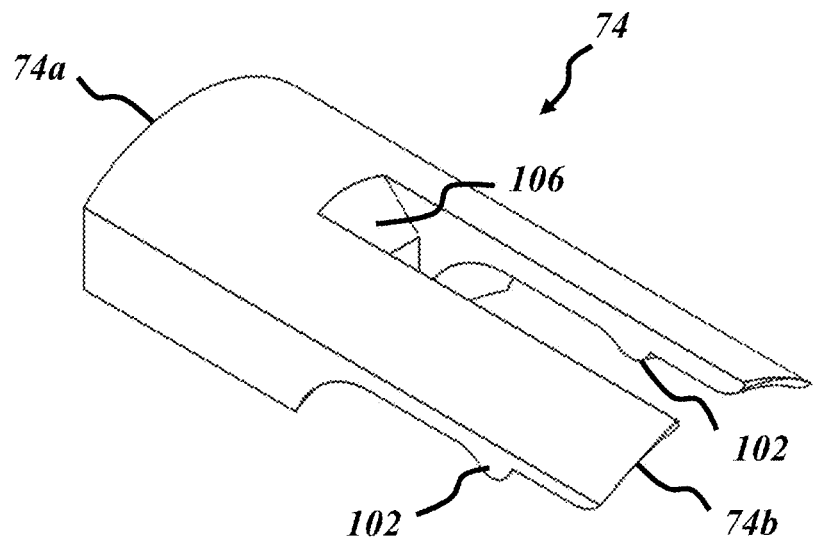
FIG. 23 is a top, right-side perspective view of the clip-closing beam of the surgical tool applicator of FIG. 1.

Referring to FIG. 20, State 1 and the enlargement of the distal end of the applicator 10 shown in corresponding FIGS. 21A and 21B, with the surgical clip 1 inserted in the applicator tube tip 38, rotation of the clip-opening trigger 40 clockwise displaces the clip-opening rod 42 proximally causing the multi-link chain 54 to rotate the clip-opening jaw 44 counter clockwise opening the surgical clip 1. As the clip-opening trigger 40 rotates clockwise from the unclamped position $\alpha_1$ (see, FIG. 26) to the central position $\alpha_2$ (see, FIG. 27), the clip-opening jaw 44 rotates from a closed position (see, FIG. 21A) in which the clip-opening jaw pivot pins 58 are in the uppermost end of the arcuate slots 60 (see, FIG. 22A) to the partially open position (see, FIG. 21B) in which the clip-opening jaw pivot pins 58 are displaced downwardly in the arcuate slots 60 (see, FIG. 22B). As the clip-opening trigger 40 rotates further clockwise from the central position (see, FIG. 27) to the over-center clamped position as (see, FIG. 28), the clip-opening jaw 44 rotates from being partially open (see, FIG. 21B) to a completely open position (see, FIG. 21C) in which the clip-opening jaw pivot pins 58 are displaced further downwardly in the arcuate slots 60 (see, FIG. 22C).

Referring to FIGS. 2, 5 and 13-16, the surgical-clip closing assembly 16 comprises a clip-closing trigger 70, a clip-closing rod 72 and a clip-closing beam 74. The clip-closing trigger 70 is pivotably attached to the hinge joint 24 of the frame-assembly hand grip 20 by a frame-assembly hinge pin 76. An upper portion 70a of the clip-closing trigger 70 extending above the hinge joint 24 has a clip-closing trigger slot 78 which receives a clip-closing slider pin 80 in the proximal end 82a of a clip-closing slider 82, the distal end 82b of which is attached to the proximal end 72a of the clip-closing rod 72 projecting proximally through the applicator tube plug 36. The bottom 82c of the clip-closing slider 82 has a slider rail 84 disposed in the frame-assembly rail slot 30 constraining the clip-closing slider 82, and therefore the clip-closing rod 72, to move along the rail longitudinal axis $R_L$ when the clip-closing trigger 70 is pivoted relative to the frame-assembly hand grip 20. Cooperating male and female leaf springs 86, 88 attached to the lower end 20b of the frame-assembly hand grip 20 and the lower end 70b the clip-closing trigger 70 respectively bias the clip-closing trigger 70 in counter-clockwise rotation relative to the frame-assembly hand grip 20. The clip-closing rod 72 is disposed in and extends the length of the applicator tube 34. The distal end 72b of the clip-closing rod 72 terminates in the applicator-tube tip 38 and has attached thereto the proximal end 74a of the clip-closing beam 74. A lower portion 70b of the of the clip-closing trigger 70 extending below the hinge joint 24 engages a ratchet rack 100 having a proximal end pivotably attached to the lower end 20b of the frame-assembly hand grip 20 and rotationally biased in the counter-clockwise direction.

Figure 24:
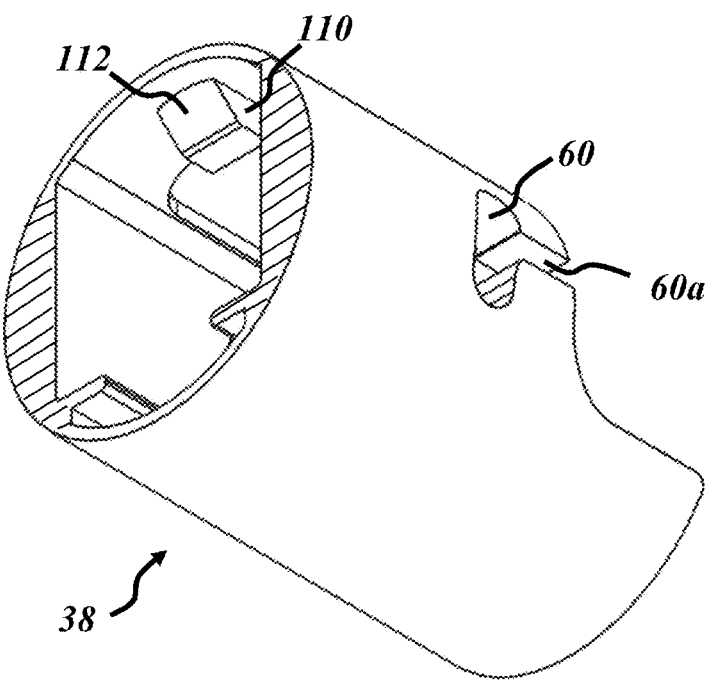
FIG. 24 is a bottom, proximal-end perspective cross-sectional view of the applicator tube tip of the surgical tool applicator of FIG. 1.

Referring to FIGS. 13-16 and 23, the clip-closing beam 74 is a beamed structure having spaced-apart clip-closing beam prongs 102 extending distally. Each clip-closing beam prong 102 has a downwardly extending clip-closing beam prong protrusion 104. A clip-closing beam ramp 106 positioned between the proximal end of the spaced-apart clip-closing beam prongs 102 has a distally-facing clip-closing beam ramp surface 108 inclined downwardly in the distal direction. The applicator-tube tip 38 has a radially inwardly extending applicator-tube ramp 110 with a proximally-facing applicator-tube ramp surface 112 inclined downwardly in the proximal direction as shown in FIG. 24. When the clip-closing trigger 70 is rotated to close the surgical clip 1, the distally-facing clip-closing beam ramp surface 108 cooperates with the proximally-facing applicator-tube ramp surface 112 to apply a bending moment to the clip-closing rod 72 causing the clip-closing beam prong protrusions 104 to apply a downward force to the clip-opening jaw 44 closing the surgical clip 1 as further discussed below.

Figure 25A:
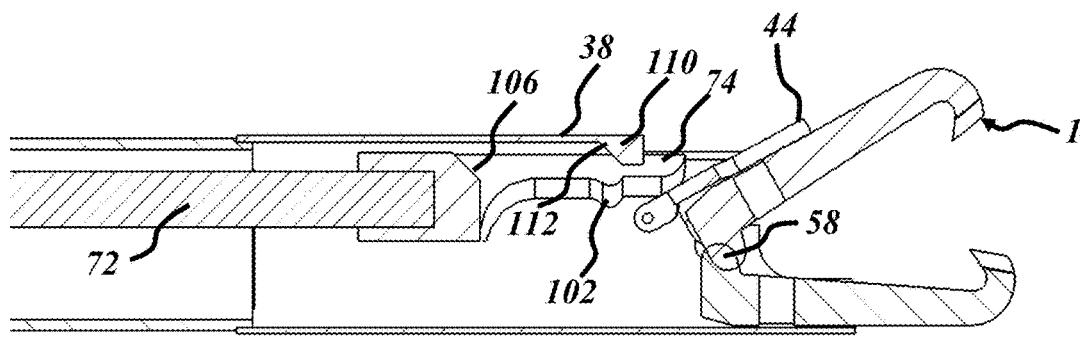
FIGS. 25A-25D are enlarged mid-plane cross-sectional elevation views of a portion of the distal end of the surgical tool applicator showing the positions of the clip-closing beam ramp relative to the applicator-tube tip ramp in FIGS. 21B-21E.
Figure 25B:
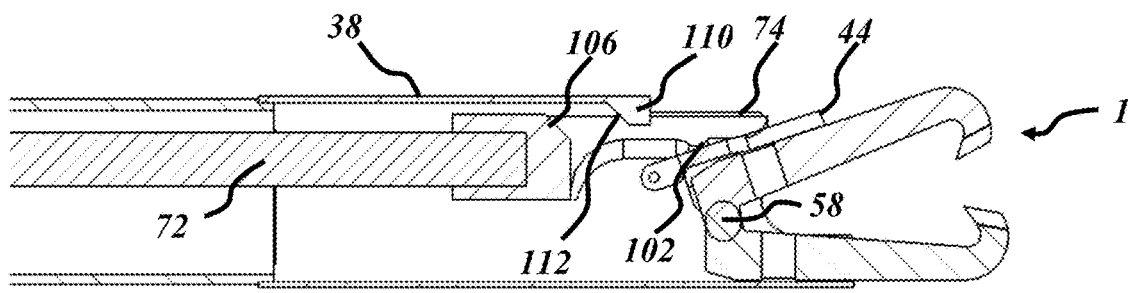
Figure 25C:
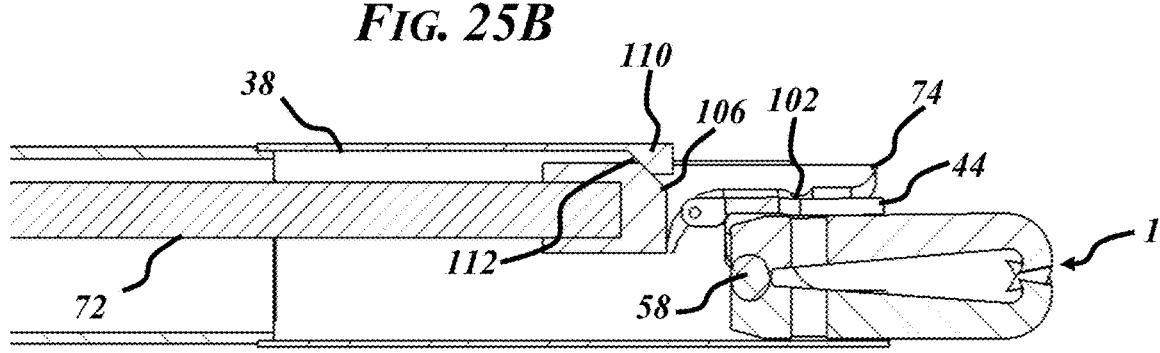
Figure 25D:
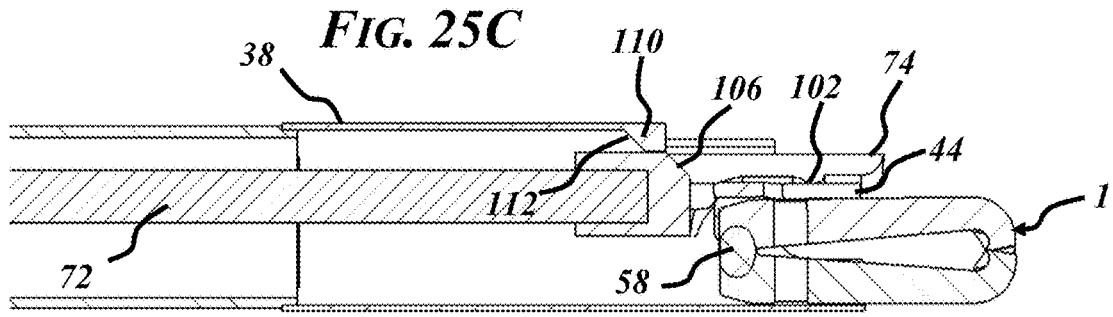

Referring to FIG. 20, States 2-4 and the enlargement of the distal end of the applicator 10 shown in corresponding FIGS. 21C, 21D and 21E, and FIGS. 25A-25D, rotation of the clip-closing trigger 70 clockwise displaces the clip-closing rod 72 distally causing the distal end 74b of the clip-closing beam 74 to contact the clip-opening jaw 44 as shown in FIG. 25A. Upon further rotation of the clip-closing trigger 70 clockwise, the continued distal displacement of the clip-closing beam 74 causes the clip-closing beam prong protrusion 104 to contact and rotate the clip-opening jaw 44 beginning the closure of the surgical clip 1 as shown in FIG. 25B. Upon still further rotation of the clip-closing trigger 70 clockwise, the continued distal displacement of the clip-closing beam 74 causes the distally-facing clip-closing beam ramp surface 108 to contact and slide along the proximally-facing applicator-tube ramp surface 112 applying a downward force to the clip-opening jaw 44 closing the surgical clip 1 as shown in FIGS. 25C and 25D.

Referring to FIGS. 6, 7 and 17-19, the surgical clip ejection assembly 18 comprises a clip ejection knob 90, a clip ejection rod 92 and a clip ejection beam 94. The clip ejection knob 90, positioned between the clip-closing slider 82 of the clip-closing assembly 16 and the proximal end 34a of the applicator tube 34, is slideably disposed on the clip-closing rod 72 which extends entirely through a clip-ejection bore 96 in the clip-ejection knob 90. A clip-ejection knob tab 98 extending downwardly from the clip-ejection knob 90 is slideably disposed in the frame-assembly rail slot 30. The clip-ejection rod 92 is disposed in and extends the length of the applicator tube 34. The proximal end 92a of the clip-ejection rod 92 projecting proximally through the applicator tube plug 36 is attached to the clip-ejection knob 90. The distal end 92b of the clip-ejection rod 92 terminates in the applicator tube tip 38 and has attached thereto the proximal end 94a of the clip ejection beam 94.

Figure 21F:
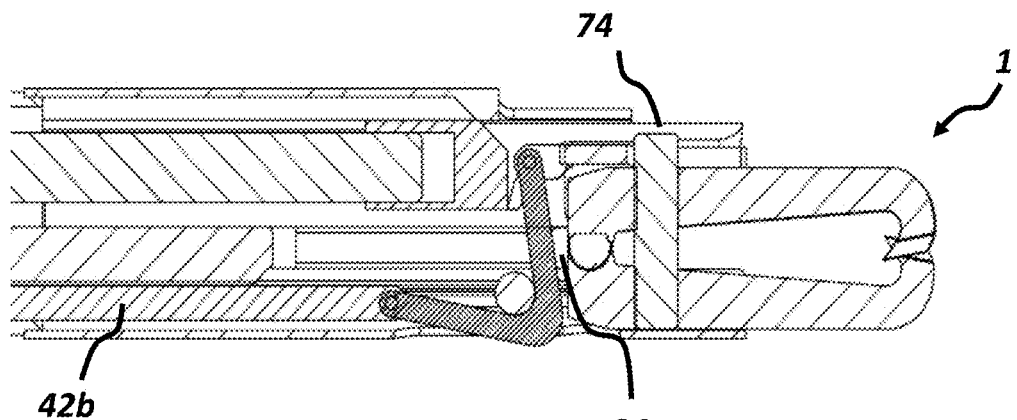
Figure 21G:
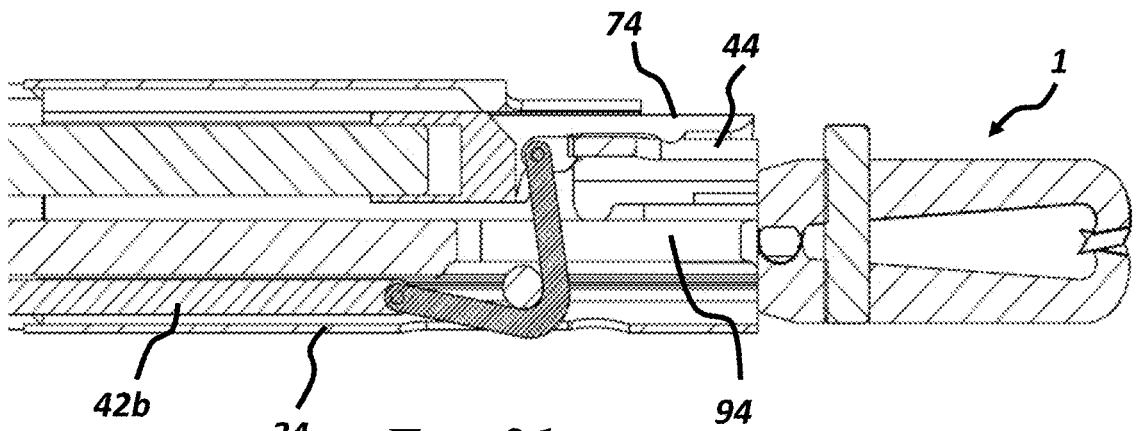

Referring to FIG. 20, States 5-7 and the enlargement of the distal end of the applicator 10 shown in corresponding FIGS. 21F and 21G, displacement of the clip-ejection knob tab 90 distally operatively couples the clip-opening jaw 44 to the applicator tube 34 and causes the clip-ejection beam 94 to eject the surgical clip 1 from the applicator 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A surgical-clip applicator (10) for applying a surgical clip (1) to a patient's tissue, the applicator (10) comprising:
    a frame assembly (12) comprising:
        an applicator tube (34) having an applicator-tube proximal end (34a) and an applicator-tube distal end (34b), the applicator-tube proximal end (34a) attached to the frame assembly (12), the applicator-tube distal end (34b) configured to releasably receive and discharge the surgical clip (1);
    a surgical-clip opening assembly (14) comprising:
        a clip-opening trigger (40) operatively coupled to the frame assembly (12);
        a clip-opening rod (42) having a clip-opening-rod proximal end (42a) and a clip-opening-rod distal end (42b), the clip-opening rod (42) disposed in the applicator tube (34), the clip-opening-rod proximal end (42a) operatively coupled to the clip-opening trigger (40); and
        a clip-opening jaw (44) operatively coupled to the applicator-tube distal end (34b) and the clip-opening-rod distal end (42b),
            wherein activation of the clip-opening trigger (40) causes displacement of the clip-opening rod (42) proximally opening the clip-opening jaw (44);
    a surgical-clip closing assembly (16) comprising:
        a clip-closing trigger (70) having a clip-closing-trigger upper end (70a) and a clip-closing-trigger lower end (70b), the clip closing trigger (70) operatively coupled to the frame assembly (12);
        a clip-closing rod (72) having a clip-closing-rod proximal end (72a) and a clip-closing-rod distal end (72b), the clip-closing rod (72) disposed in the applicator tube (34), the clip-closing-rod proximal end (72a) operatively coupled to the clip-closing trigger (40); and
        a clip-closing beam (74) attached to the clip-closing-rod distal end (72b),
            wherein activation of the clip-closing trigger (70) causes displacement of the clip-closing rod (72) distally causes the clip-closing beam (74) to close the clip-opening jaw (44); and
    a surgical-clip ejection assembly (18) comprising:
        a clip-ejection knob (90) slideably disposed on the clip-closing rod (72), the clip-ejection knob (90) having a clip-ejection-knob tab (98) operatively coupled to the frame assembly (12);
        a clip-ejection rod (92) having a clip-ejection-rod proximal end (92a) and a clip-ejection-rod distal end (92b), the clip-ejection rod (92) disposed in the applicator tube (34), the clip-ejection-rod proximal end (92a) operatively coupled to the clip-ejection knob (90); and
        a clip-ejection beam (94) attached to the clip-ejection-rod distal end (92b),
            wherein activation of the clip-ejection-knob tab (90) causes displacement of the clip-ejection beam (94) distally ejecting the surgical clip (1) from the applicator (10) when the surgical clip (1) is releasably retained in the applicator-tube distal end (34b),
    wherein the surgical-clip opening assembly (14), the surgical-clip closing assembly (16), and the surgical-clip ejection assembly (18) are independently activatable.

2. The surgical-clip applicator (10) according to claim 1, wherein the frame assembly (12) further comprising;
    a frame-assembly hand-grip (20) having a frame-assembly hand-grip upper end (20a) and a frame-assembly hand-grip lower end (20b);
    a frame-assembly rail (22) having a frame-assembly-rail proximal end (22a) and a frame-assembly-rail distal end (22b), the frame-assembly-rail proximal end (22a) extending along a longitudinal rail axis ($R_L$) at an obtuse angle (α) relative to the frame-assembly hand-grip (20),
    wherein the applicator-tube proximal end (34a) is fixedly attached to the frame-assembly rail (22) and the applicator-tube distal end (34b) extends beyond the frame-assembly-rail distal end (22b).

3. The surgical-clip applicator (10) according to claim 2, wherein the clip-closing trigger (70) is pivotably attached to the frame-assembly hand-grip (20), the surgical-clip opening assembly has a clip-closing slider (82) slideably attached to the frame-assembly rail (22), the clip-closing slider (82) has a clip-closing-slider proximal end (82a) attached to the clip-closing-trigger upper end (70a) and a clip-closing-slider distal end (82b) attached to the clip-closing-rod proximal (72a), and wherein the clip-closing rod (72) moves along the rail longitudinal axis ($R_L$) when the clip-closing trigger (70) is pivoted relative to the frame-assembly hand-grip (20).

4. The surgical-clip applicator (10) according to claim 2, wherein cooperating male and female leaf springs (86, 88) attached to the frame-assembly hand-grip lower end (20b) and the clip-closing-trigger lower end (70b) respectively bias the clip-closing trigger (70) in counter-clockwise rotation relative to the frame-assembly hand grip (20).

5. The surgical-clip applicator (10) according to claim 1, wherein the applicator-tube distal end (34b) is configured as a removable applicator-tube tip (38) having an applicator-tube-tip distal end (38b) configured to receive the surgical clip (1).

6. The surgical-clip applicator (10) according to claim 1, wherein the clip-opening trigger (40) is a toggle clamp having an unclamped position ($\alpha_1$) in which no force is applied by the clip-opening trigger (40) to the clip-opening jaw (44), a central position ($\alpha_2$) in which a force applied to the clip-opening trigger (40) opens the clip-opening jaw (44) and an over-center, clamped position ($\alpha_3$) in which the clip-opening trigger (40), and the clip-opening jaw (44), in turn, are locked in the open position.

7. The surgical-clip applicator (10) according to claim 1, wherein the clip-opening-rod distal end (42b) is coupled to the clip-opening jaw (44) by a flexible link.

8. The surgical-clip applicator (10) according to claim 1, wherein the clip-opening jaw (44) is a beamed structure having spaced-apart clip-opening-jaw prongs (56) extending distally and configured to releasably receive a first clamping arm (2) of the surgical clip (1).

9. The surgical-clip applicator (10) according to claim 8, wherein the applicator-tube distal end (34b) is configured as a removable applicator-tube tip (38) having an applicator-tube-tip distal end (38b) configured to receive the surgical clip (1) and clip-opening-jaw pivot pins (58) extending outwardly from each clip-opening-jaw prong (56) engage diametrically-opposed circumferentially-elongated arcuate slots (60) in a side wall of the applicator-tube tip (38).

10. The surgical-clip applicator (10) according to claim 9, wherein the arcuate slots (60) are spaced from the applicator-tube-tip distal end (38b) such that the clip-opening-jaw prongs (56) are in register with corresponding diametrically-opposed mounts (62) extending inwardly from the side wall of the applicator-tube tip (38) and configured to form a fixed jaw releasably receiving a second clamping arm (3) of the surgical clip (1).

11. The surgical-clip applicator (10) according to claim 1, wherein the clip-closing beam (74) further comprises:
   spaced-apart clip-closing-beam prongs (102) extending distally, each clip-closing-beam prong (102) having a downwardly extending clip-closing beam-prong protrusion (104); and
   a clip-closing beam ramp (106) positioned between the proximal end of the spaced-apart clip-closing beam prongs (102), the clip-closing beam ramp (106) having a distally-facing clip-closing beam-ramp surface (108) inclined downwardly in the distal direction,
   wherein the applicator-tube distal end (34b) is configured as a removable applicator-tube tip (38) having a radially inwardly extending applicator-tube ramp (110) with a proximally-facing applicator-tube ramp surface (112) inclined downwardly in the proximal direction, and
   wherein when the clip-closing trigger (70) is rotated, the distally-facing clip-closing beam ramp surface (108) cooperates with the proximally-facing applicator-tube ramp surface (112) to apply a bending moment to the clip-closing rod (72) causing the clip-closing beam prong protrusions (104) to apply a downward force to the clip-opening jaw (44).

* * * * *